US009646806B2

(12) United States Patent
Jang et al.

(10) Patent No.: US 9,646,806 B2
(45) Date of Patent: May 9, 2017

(54) PLASMA ELECTRODE DEVICE AND METHOD FOR MANUFACTURING THE SAME

(71) Applicant: LG ELECTRONICS INC., Seoul (KR)

(72) Inventors: Jaesoo Jang, Seoul (KR); Bongjo Sung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 115 days.

(21) Appl. No.: 14/660,126

(22) Filed: Mar. 17, 2015

(65) Prior Publication Data

US 2015/0279622 A1    Oct. 1, 2015

(30) Foreign Application Priority Data

Mar. 25, 2014  (KR) .................. 10-2014-0034441

(51) Int. Cl.
*H01J 37/32*  (2006.01)
*A61L 2/08*   (2006.01)
(Continued)

(52) U.S. Cl.
CPC ........ *H01J 37/32055* (2013.01); *A61L 2/088* (2013.01); *A61L 9/22* (2013.01);
(Continued)

(58) Field of Classification Search
CPC ............ H01J 37/32055; H01J 37/3244; B01D 53/323; B01D 2257/708; B01D 2257/91;
(Continued)

(56) References Cited

U.S. PATENT DOCUMENTS 3,976,031 A    8/1976  Itoh
7,258,730 B2   8/2007  Choi et al.
(Continued)

FOREIGN PATENT DOCUMENTS

CN    1654111    8/2005
CN    1749662    3/2006
(Continued)

OTHER PUBLICATIONS

Extended European Search Report for Application 15176811.6 dated Dec. 3, 2015.
(Continued)

*Primary Examiner* — Donald Raleigh
*Assistant Examiner* — Kevin Quarterman
(74) *Attorney, Agent, or Firm* — KED & Associates LLP

(57) ABSTRACT

Provided are a plasma electrode device and a manufacturing method thereof. The plasma electrode device includes a first substrate including a first substrate main body having a first flow hole through which air flows and a first discharge electrode disposed on one surface of the first substrate main body and a second substrate disposed on one side of the first substrate, the second substrate including a second flow hole through which air flows and a second discharge electrode acting with the first substrate. The first substrate main body includes a ground electrode acting with the first or second discharge electrode to perform plasma discharge and a first insulator coupled to the ground electrode.

19 Claims, 7 Drawing Sheets

(51) Int. Cl.
| | |
|---|---|
| *B01J 19/12* | (2006.01) |
| *A61L 9/22* | (2006.01) |
| *B01D 53/32* | (2006.01) |
| *F24F 3/16* | (2006.01) |
| *B01D 53/86* | (2006.01) |

(52) U.S. Cl.
CPC .......... *B01D 53/323* (2013.01); *B01J 19/127* (2013.01); *H01J 37/3244* (2013.01); *B01D 53/8675* (2013.01); *B01D 2257/504* (2013.01); *B01D 2257/708* (2013.01); *B01D 2257/91* (2013.01); *B01D 2259/4508* (2013.01); *B01J 2219/0894* (2013.01); *B01J 2219/1203* (2013.01); *F24F 3/166* (2013.01)

(58) Field of Classification Search
CPC ........ B01D 2259/4508; B01D 53/8675; B01D 2257/504; A61L 9/22; A61L 2/088; B01J 19/127; B01J 2219/0894; B01J 2219/1203; F24F 3/166
See application file for complete search history.

(56) References Cited

U.S. PATENT DOCUMENTS

| | | | |
|---|---|---|---|
| 7,261,767 | B2 | 8/2007 | Choi et al. |
| 7,294,176 | B2 | 11/2007 | Kim et al. |
| 7,722,707 | B2 | 5/2010 | Tanaka et al. |
| 2002/0179579 | A1 | 12/2002 | Lin et al. |
| 2004/0145853 | A1 | 7/2004 | Sekoguchi et al. |
| 2005/0118079 | A1 | 6/2005 | Muroi et al. |
| 2005/0257687 | A1 | 11/2005 | Tanaka et al. |
| 2006/0056129 | A1 | 3/2006 | Kim et al. |
| 2006/0070526 | A1 | 4/2006 | Hong et al. |
| 2006/0146472 | A1 | 7/2006 | Van Beek et al. |
| 2008/0120989 | A1 | 5/2008 | Tanaka et al. |
| 2008/0170971 | A1 | 7/2008 | Bergeron et al. |
| 2008/0179286 | A1 | 7/2008 | Murokh |
| 2009/0207548 | A1 | 8/2009 | Seto et al. |
| 2009/0223806 | A1 | 9/2009 | Thevenet et al. |
| 2010/0072777 | A1 | 3/2010 | Ramsay |
| 2010/0072778 | A1 | 3/2010 | Ramsay |
| 2010/0308332 | A1 | 12/2010 | Ono et al. |
| 2011/0001425 | A1 | 1/2011 | Murata et al. |
| 2011/0298376 | A1* | 12/2011 | Kanegae ................ B01J 19/088 315/111.51 |
| 2012/0168082 | A1* | 7/2012 | Izuo ........................ C23C 16/24 156/345.44 |
| 2012/0269677 | A1 | 10/2012 | Zhou et al. |
| 2013/0119264 | A1 | 5/2013 | Yagi et al. |

FOREIGN PATENT DOCUMENTS

| | | |
|---|---|---|
| CN | 2930194 | 8/2007 |
| CN | 201306203 | 9/2009 |
| CN | 102059106 | 5/2011 |
| CN | 102896113 | 1/2013 |
| CN | 202666618 | 1/2013 |
| EP | 1 547 693 A1 | 6/2005 |
| EP | 1 980 317 A1 | 10/2008 |
| EP | 2 923 752 A1 | 9/2015 |
| JP | 2010-033867 | 12/2010 |
| JP | 2013-258137 | 12/2013 |
| KR | 10-2004-0073482 | 9/2004 |
| KR | 100657476 B1 | 12/2006 |
| WO | WO 2007/070704 A2 | 6/2007 |
| WO | WO 2012/005386 | 1/2012 |
| WO | WO2013/085045 | 6/2013 |
| WO | WO 2013/085845 | 6/2013 |

OTHER PUBLICATIONS

Partial European Search Report for Application EP 15 17 6824 dated Nov. 12, 2015.
United States Office Action dated Jan. 19, 2017 issued in co-pending U.S. Appl. No. 14/799,885.
Chinese Office Action dated Dec. 29, 2016 issued in Application No. 201510032591.5 (English translation attached).

* cited by examiner

PLASMA ELECTRODE DEVICE AND METHOD FOR MANUFACTURING THE SAME

CROSS-REFERENCE TO RELATED APPLICATIONS

The present application claims priority under 35 U.S.C. 119 and 35 U.S.C. 365 to Korean Patent Application No. 10-2014-0034441 (filed on Mar. 25, 2014), which is hereby incorporated by reference in its entirety.

BACKGROUND

The present disclosure relates to a plasma electrode device.

Recently, constructed buildings receive minimum external air and are sealed off from the outside for energy saving, and thus air pollution therein becomes more serious. Accordingly, mandatory regulations for indoor pollutants are being increasingly reinforced.

Meanwhile, during operations of home appliances installed at home or offices, indoor pollutants may be stuck to or discharged from the home appliances. The indoor pollutants may cause unpleasant smells and have a negative influence on user's health. For example, in the case of home appliances, such as air conditioners, dehumidifiers, air cleaners, refrigerators, and washing machines, which use air containing moisture or water, contamination due to dust or microorganisms may occur inside or outside the home appliances.

More specifically, the indoor pollutants may be classified into (1) particulate pollutants such as fine dust and asbestos, (2) gaseous pollutants such as carbon dioxide, formaldehyde, and volatile organic compounds (VOC), and (3) biological pollutants such as virus, fungi, and bacteria.

Surface discharge plasma chemical processing may be used to remove such indoor pollutants. In general, in the surface discharge plasma chemical processing, high intensity plasma is generated on a device surface by high frequency discharge using ceramics to generate a large amount of OH radicals, and then the pollutants are removed by the OH radicals and ozone in the plasma.

One example of the following technique (hereinafter, referred to as "the related art") is disclosed in Korean Patent No. 10-0657476 (issued on Dec. 7, 2006 and entitled "Surface discharge type air cleaning device") filed by the present applicant.

The air cleaning device according to the related art includes a discharge electrode provided on a top surface of two sheet of insulating dielectrics that are attached to each other, a ground electrode interposed between the two sheet of insulating dielectrics, and a coating layer sealing the discharge electrode to prevent the discharge electrode from being directly exposed to the air. Here, each of the insulating dielectrics may be coated with an insulating material. For example, the insulating material includes ceramics.

When the insulating dielectric is coated with the insulating material or includes the coating layer, the surface of the electrode has to be uniformly coated to generate uniform discharge. However, in the case of the plasma electrode device according to the related art, it is very difficult to form the coating having a uniform thickness, and uneven patterns beyond an allowable range are formed on the surface in the coating process.

In addition, the plasma electrode device according to the related art may generate an insufficient amount of ions, and thus it may be difficult to remove effectively pollutants. Further, a large amount of ozone that is harmful to humans may be generated during the plasma discharge.

SUMMARY

Embodiments provide a plasma electrode device that is capable of removing pollutants.

In one embodiment, a plasma electrode device includes: a first substrate including a first substrate main body having a first flow hole through which air flows and a first discharge electrode disposed on one surface of the first substrate main body; and a second substrate disposed on one side of the first substrate, the second substrate including a second flow hole through which air flows and a second discharge electrode acting with the first substrate, wherein the first substrate main body includes: a ground electrode acting with the first or second discharge electrode to perform plasma discharge; and a first insulator coupled to the ground electrode.

The first insulator may be disposed to surround the ground electrode.

The first insulator may include: a first base on which the ground electrode is seated; a first side surface part extending from each of both sides of the first base to surround a side surface of the ground electrode; and a first top surface part extending from the first side surface part to cover a top surface of the ground electrode.

The second substrate may include a second insulator surrounding the second discharge electrode.

The second insulator may include: a second base on which the second discharge electrode is seated; a second side surface part extending from each of both sides of the second base to surround a side surface of the second discharge electrode; and a second top surface part extending from the second side surface part to cover a top surface of the second discharge electrode.

A distance formation part may be disposed between the first and second substrates to allow the second substrate to be spaced a predetermined distance (d) from the first substrate.

The predetermined distance (d) may have a value of several micrometers ($\mu$m).

The first or second insulator may be formed of an epoxy resin.

A photocatalyst activated by visible light to decompose a pollutant or reduce ozone may be disposed between the first insulator and the first discharge electrode.

The photocatalyst may include silver phosphate ($Ag_3PO_4$), titanium dioxide ($TiO_2$), and inorganic binder.

The first flow hole may be provided in plurality, and the second flow hole may have the same number as the plurality of flow holes to communicate with the first flow holes.

The first discharge electrode may include: a discharge electrode to which electric power is applied; a pattern frame surrounding the first flow hole and having a preset shape; and at least one discharge needle provided on the pattern frame.

The first flow hole may be provided in plurality, and the pattern frame may be disposed to surround a portion of the plurality of first flow holes.

In another embodiment, a method for manufacturing a plasma electrode device include: manufacturing a first substrate, wherein the manufacturing of the first substrate includes: disposing a ground electrode on a bottom surface part of a first insulator; covering the ground electrode by using side and top surface parts of the first insulator;

disposing a photocatalyst on the first insulator; and disposing a first discharge electrode on the photocatalyst.

The method may further include: manufacturing a second substrate; and spacing the second substrate apart from the first substrate by a distance corresponding to a distance formation part, wherein the manufacturing of the second substrate may include: disposing a second discharge electrode on a bottom surface part of a second insulator; and covering side and top surfaces of the second discharge electrode, which are exposed to the outside, with side and top surface parts of the second insulator.

In further another embodiment, a plasma electrode device includes: a first substrate provided with a first substrate main body including a ground electrode and a photocatalyst and a first discharge electrode disposed on one surface of the first substrate main body; a first insulator provided on the first substrate main body to surround the ground electrode; a second substrate disposed on one side of the first substrate, the second substrate including a second substrate main body provided with a second discharge electrode acting with the ground electrode; a second insulator provided on the second substrate main body to surround the second discharge electrode; and a distance formation part spacing the first substrate apart from the second substrate.

The first substrate may further include a first substrate main body having a plurality of first flow holes through which air flows, and the first discharge electrode may be disposed on one surface of the first substrate main body.

The first discharge electrode may include: a discharge electrode to which electric power is applied; a pattern frame disposed outside the first flow holes, and the pattern frame having a closed shape; and at least one discharge needle protruding from an outer circumferential surface of the pattern frame.

The pattern frame may have one of circular, oval, and polygonal shapes.

A plurality of second flow holes may be defined in the second substrate main body to correspond to the plurality of first flow holes.

The details of one or more embodiments are set forth in the accompanying drawings and the description below. Other features will be apparent from the description and drawings, and from the claims.

DETAILED DESCRIPTION OF THE EMBODIMENTS

Hereinafter, exemplary embodiments will be described with reference to the accompanying drawings. However, the spirit of the present disclosure is not limited to the disclosed embodiments, and those skilled in the art that understands the spirit of the present disclosure will be able to readily propose other embodiments without departing from the spirit and scope of the present disclosure.

Figure 1:
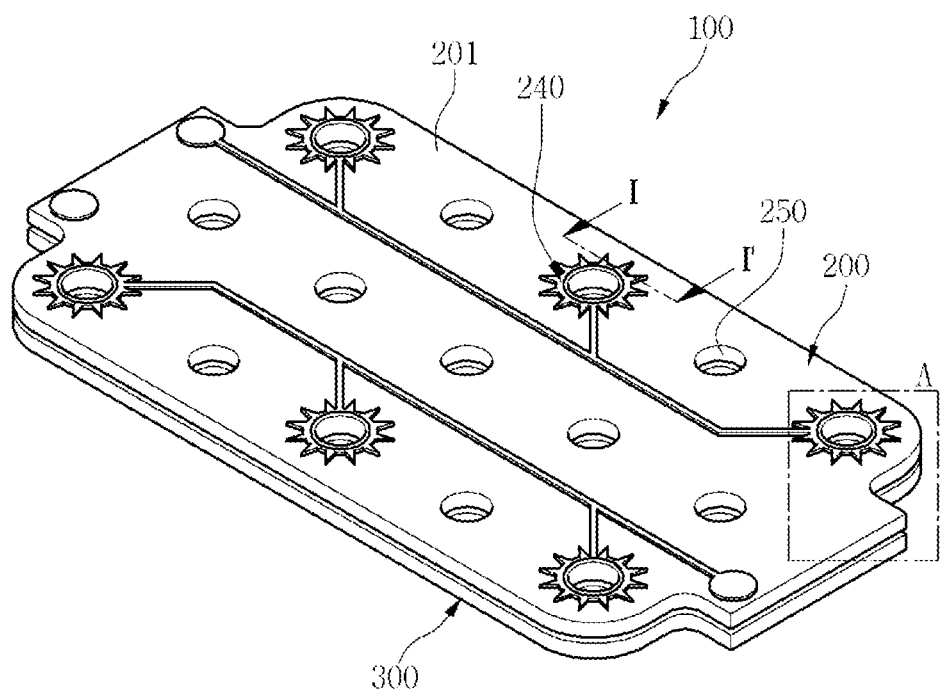
FIG. 1 is a perspective view of a plasma electrode device according to an embodiment.
Figure 2:
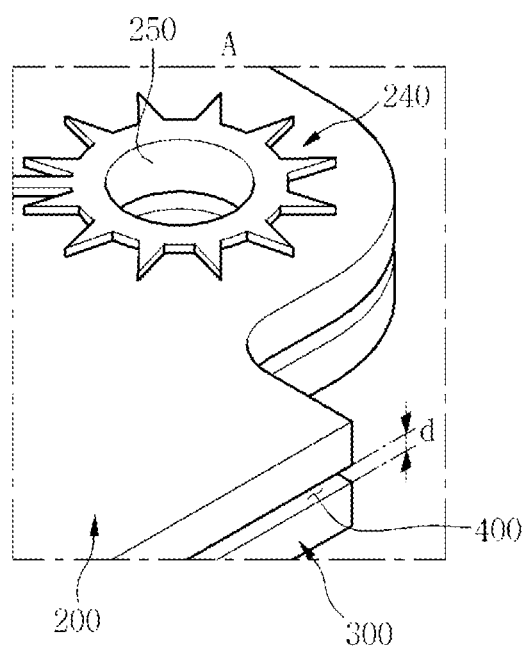
FIG. 2 is an enlarged view of a portion "A" of FIG. 1.
Figure 3:
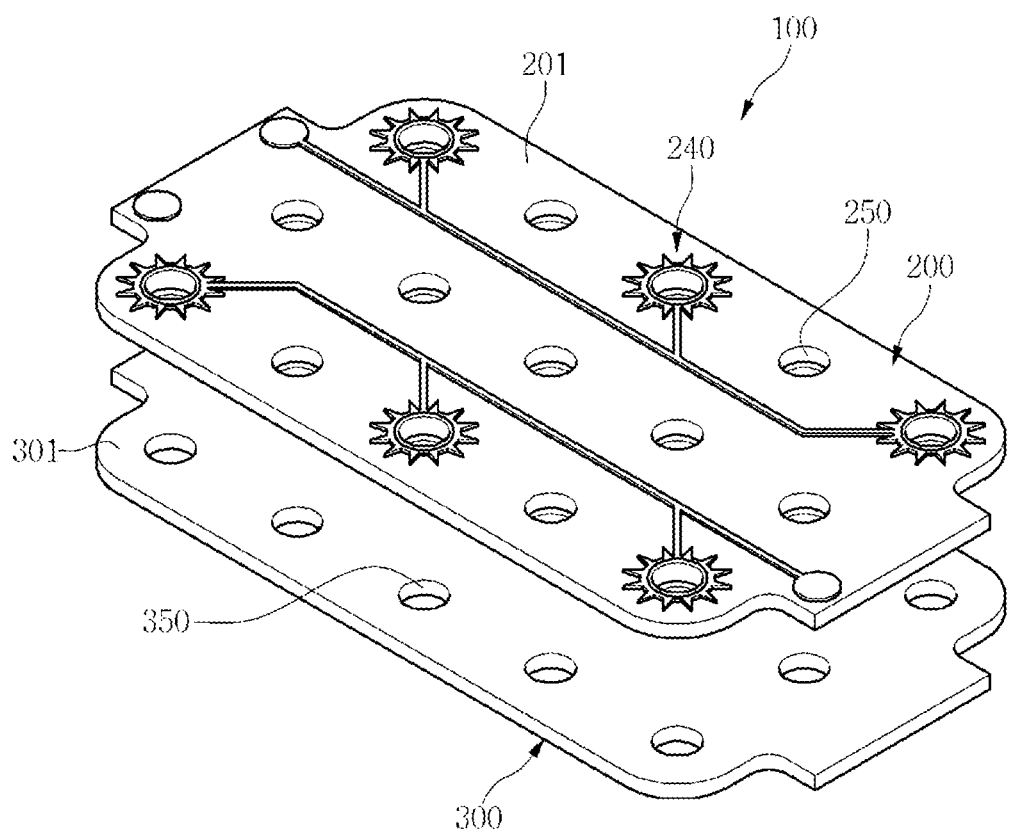
FIG. 3 is an exploded perspective view of the plasma electrode device according to the embodiment.

FIG. 1 is a perspective view of a plasma electrode device according to an embodiment, FIG. 2 is an enlarged view of a portion "A" of FIG. 1, and FIG. 3 is an exploded perspective view of the plasma electrode device according to the embodiment.

Referring to FIGS. 1 to 3, a plasma electrode device 100 according to an embodiment includes first and second substrates 200 and 300 facing each other. For example, the second substrate 300 may be disposed below the first substrate 200 and have the same size and shape as the first substrate 200. The first and second substrates 200 and 300 may be referred to as an "upper plate" and a "lower plate", respectively.

In detail, a distance formation part 400 is interposed between the first and second substrates 200 and 300 such that the first and second substrates 200 and 300 are spaced a predetermined distance (d) apart from each other. For example, the predetermined distance (d) may have a value of several micrometers (μm).

Figure 4:
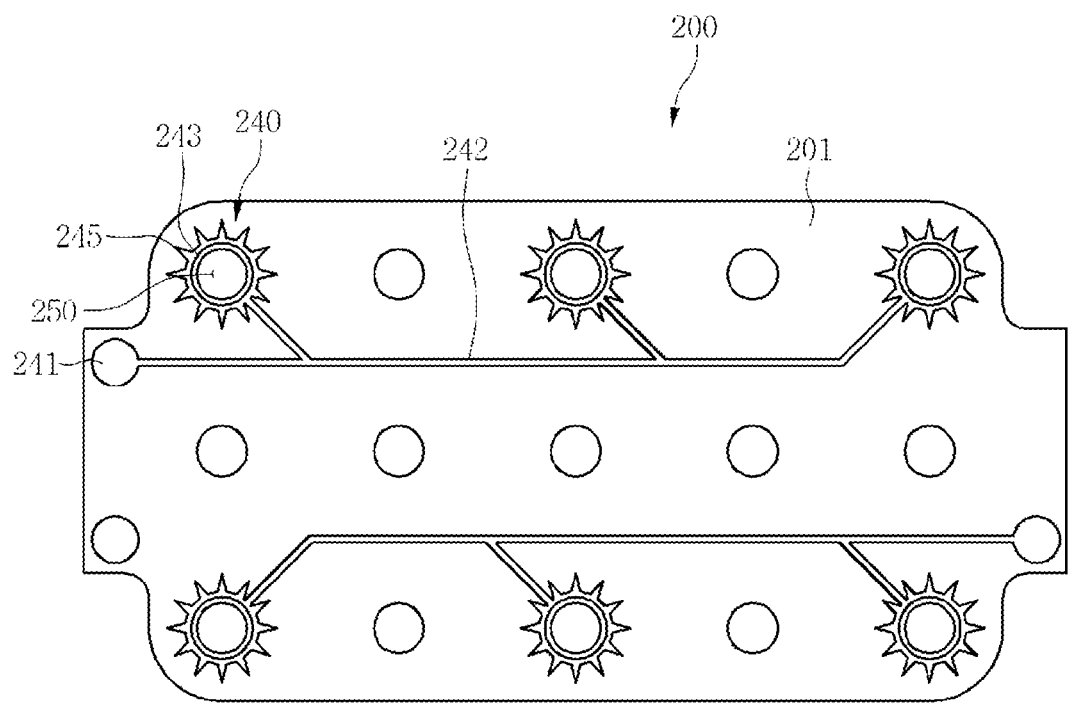
FIG. 4 is a plan view of a first substrate according to an embodiment.

The first substrate 200 includes a first substrate main body 201 having an approximately rectangular plate shape and at least one first flow hole 250 passing through the first substrate main body 201 to guide an air flow. The first flow hole 250 may be provided in plurality. For example, a total of fifteen first flow holes 250 may be provided as illustrated in FIG. 4.

The first substrate 200 includes a first discharge electrode 240 provided with a pattern frame 243 (see FIG. 4) disposed to surround at least a portion of the plurality of first flow holes 250. The pattern frame 243 may be configured to surround a portion of the plurality of first flow holes 250. For example, the pattern frame 243 may be configured to surround six first flow holes 250 of the fifteen first flow holes 250.

Figure 5:
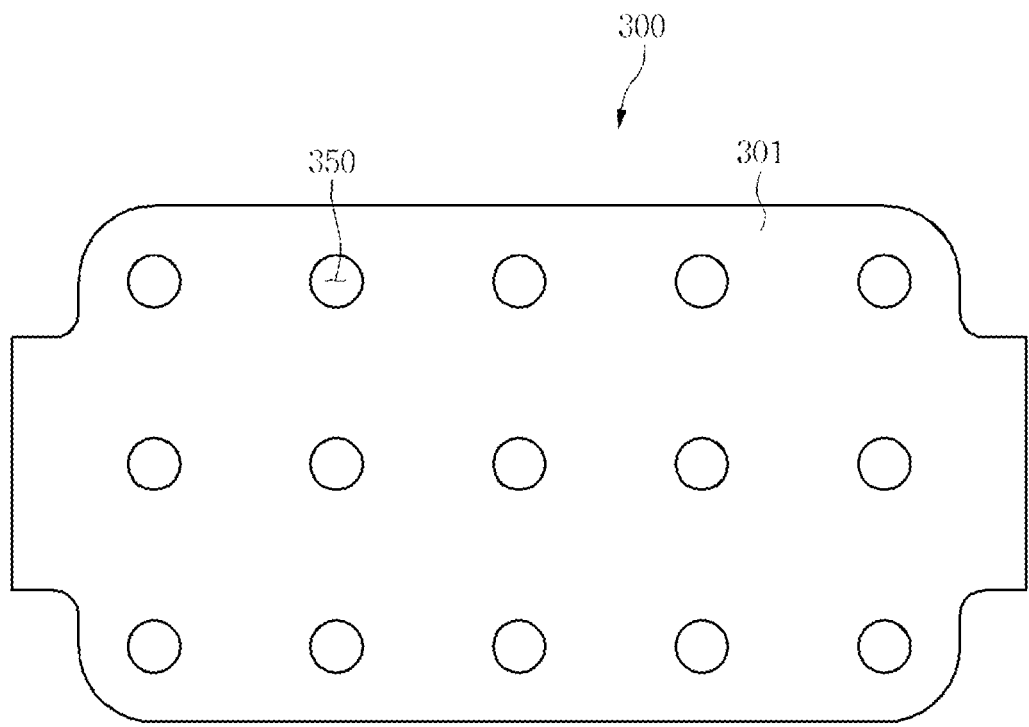
FIG. 5 is a plan view of a second substrate according to an embodiment.

The second substrate 300 includes a second substrate main body 301 having an approximately rectangular plate shape and at least one second flow hole 350 passing through the second substrate main body 301 to guide an air flow. The second flow hole 350 may be provided in plurality. For example, like the first flow hole 250, a total of fifteen second flow holes 350 may be provided as illustrated in FIG. 5. The plurality of second flow holes 350 may be positioned below the first flow holes 250 to communicate with the first flow holes 250, respectively.

When the plasma electrode device 100 operates to generate plasma discharge, air passing through the first and second flow holes 250 and 350 may be oxidized or decomposed.

Figure 6:
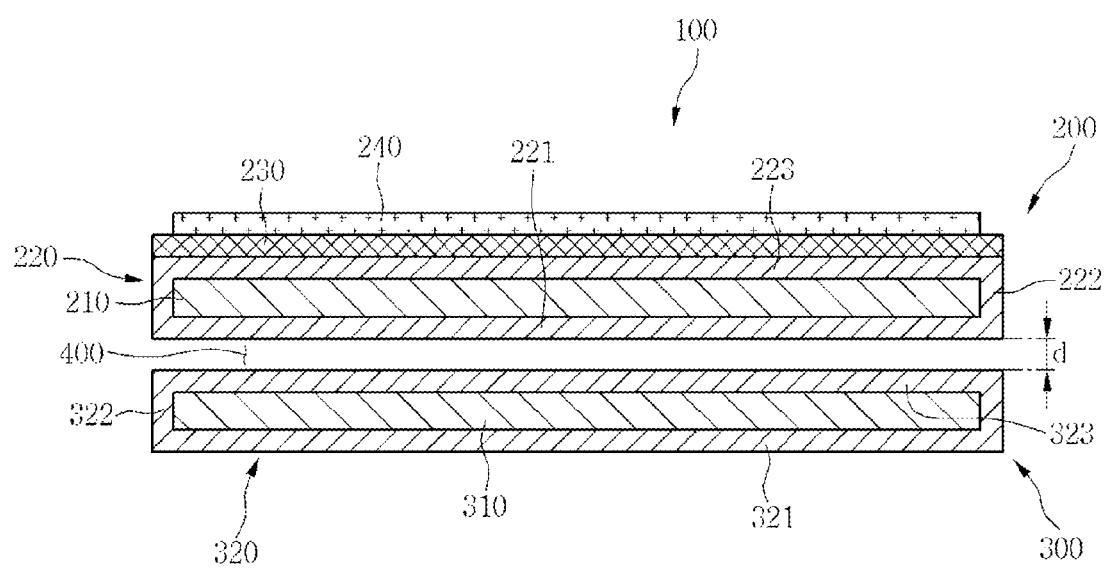
FIG. 6 is a cross-sectional view taken along line I-I' of FIG. 1.

FIG. 4 is a plan view of the first substrate according to the embodiment, FIG. 5 is a plan view of the second substrate according to the embodiment, and FIG. 6 is a cross-sectional view taken along line I-I' of FIG. 1.

Referring to FIGS. 4 and 6, the first substrate 200 according to the embodiment includes the first substrate main body 201 in which the plurality of first flow holes 250 are defined and the first discharge electrode 240 provided on one surface of the first substrate main body 201.

The first substrate main body 201 includes a ground electrode 210, a first insulator 220 surrounding the ground electrode 210, and a photocatalyst 230 provided on at least one surface of the first insulator 220.

The first discharge electrode 240 includes a discharge electrode 241 to which electric power is applied, the pattern frame 243 surrounding at least one portion of plurality of first flow holes 250, and at least one discharge needle 245 provided on the pattern frame 243.

The pattern frame 243 may be provided in plurality and has a closed shape surrounding the first flow hole 250. For example, the pattern frame may have a shape such as a circular, oval, or polygonal shape. The discharge needle 245 protrudes from an outer circumferential surface of the pattern frame 243.

The first discharge electrode 240 includes a connection line 242 extending from the discharge electrode 241 to the plurality of pattern frames 243. The connection line 242 may be branched from the discharge electrode 241 toward the pattern frames 243.

Metal oxide paste may be printed on the first discharge electrode 240. A metallic material of the metal oxide paste may be selected from the group consisting of tungsten, iron, copper, platinum, and silver. For example, the metallic material may be silver (Ag).

For example, silver oxide paste may be printed on the first discharge electrode 240. Since the silver oxide paste has a low resistance of about 10Ω to about 20Ω, the discharge may easily occur due to the low resistance to generate uniform discharge on the entire electrode. In addition, the silver oxide paste may reduce an amount of ozone by discharge.

Referring to FIG. 5, the second substrate 300 according to the embodiment includes the second substrate main body 301 in which the plurality of second flow holes 350 are defined. The second substrate main body 301 includes a second discharge electrode 310 and a second insulator 320 surrounding the second discharge electrode 310. The constitutions of the first and second substrate main bodies 201 and 301 will be described below in detail.

Figure 7:
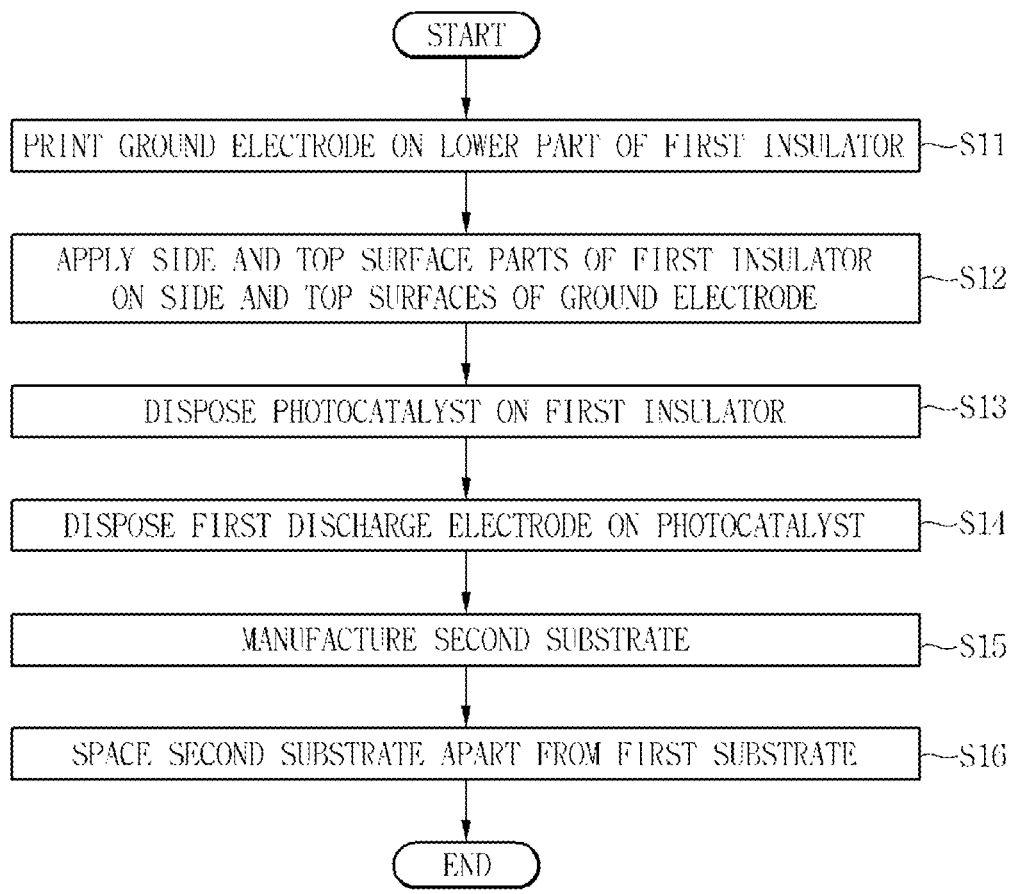
FIG. 7 is a flowchart illustrating a method of manufacturing a plasma electrode device according to an embodiment.

FIG. 7 is a flowchart illustrating a method of manufacturing a plasma electrode device according to an embodiment.

Referring to FIGS. 6 and 7, the first substrate main body 201 of the first substrate 200 according to the embodiment includes the ground electrode 210 acting with the first or second discharge electrode 240 or 310 to generate plasma discharge and the first insulator 220 surrounding the ground electrode 210 to prevent the ground electrode 210 from being exposed to the outside.

The ground electrode 210 may be provided as a metal plate, for example formed of copper (Cu), and the first insulator 220 may be formed of an epoxy resin. The first insulator 220 may be disposed to surround both side surfaces and top and bottom surfaces of the ground electrode 210.

In detail, the first insulator 220 includes a bottom surface part 221 on which the ground electrode 210 is seated, side surface parts 222 extending upward from each of both sides of the bottom surface part 221, and an top surface part 223 covering an upper side of the side surface part 222. An outer surface of the ground electrode 210 is completely surrounded by the bottom, side, and top surface parts 221, 222, and 223 of the first insulator 220.

A method of manufacturing the ground electrode 210 and the first insulator 220 will be described below in brief.

The ground electrode 210 is masked on the bottom surface part 221 of the first insulator 220. Here, the bottom surface part 221 is formed of an epoxy resin and may be understood as a base on which the ground electrode 210 is disposed (S11).

When the ground electrode 210 is marked, a lower surface of the ground electrode 210 is covered by the first insulator 220, and side and top surfaces of the ground electrode 210 are exposed to the outside.

The side and top surface parts 222 and 223 of the first insulator 220 are coated on the side and top surfaces of the ground electrode 210 exposed to the outside. In this case, the coated side and top surface parts 222 and 223 may be formed of the same epoxy resin as the bottom surface part 221 (S12).

The photocatalyst 230, which reacts with or is activated by visible light, is disposed on the first insulator 220 (S13). In other words, the photocatalyst 230 is interposed between the first insulator 220 and the first discharge electrode 240. The photocatalyst 230 may easily decompose various harmful substances, perform antibacterial and germicidal functions, and reduce ozone.

The visible light is understood as light emitted from an external light source disposed outside the plasma electrode device 100. For example, the visible light may include natural light or light emitted from a lighting source existing in a predetermined space.

The photocatalyst 230 includes a variety of compositions. In detail, the compositions may include silver phosphate ($Ag_3PO_4$), titanium dioxide ($TiO_2$) and inorganic binder. For example, the photocatalyst 230 may include about 20 parts to about 50 parts by weight of silver phosphate ($Ag_3PO_4$), about 5 parts to about 40 parts by weight of titanium dioxide ($TiO_2$), and about 10 parts to about 40 parts by weight of inorganic binder.

The titanium dioxide ($TiO_2$) may exhibit high activity under ultraviolet radiation and be stable chemically without being eroded by acidic, alkaline, and an organic solvent.

The silver phosphate ($Ag_3PO_4$) may undergo catalytic activity reaction by light energy of visible light in a wavelength band of about 385 nm or more, an average wavelength of which is about 500 nm. The titanium dioxide is mixed with the silver phosphate so that the photocatalyst is effectively activated by the visible light. In addition, the silver phosphate may have a synergy effect of decomposing organic matters (microorganisms and stinking components) through simultaneous activation with titanium dioxide in a low-energy region (in the visible-light wavelength region), in addition to antibacterial performance itself against bacteria, fungi, and the like.

The inorganic binder includes a poly-silicate compound. The poly-silicate compound may consist of colloidal silica ($SiO_2$) and metal alkoxide. In addition, the inorganic binder may additionally include other components. The other components may be selected by those skilled in the art in consideration of characteristics of a finally produced coating composition. For example, the other components may include a stabilizer, an acid catalyst, a curing agent, a metallic additive, and the like.

The stabilizer may be selected from the group consisting of acetylacetone, ethyl acetoacetate, iron acetylacetone, alkanolamine, and combinations thereof. The inorganic binder may include about 0.1 parts to about 0.5 parts by weight of the stabilizer.

The acid catalyst may be selected from the group consisting of a phosphoric acid metal catalyst, a hydrochloric acid metal catalyst, a nitric acid metal catalyst, a phosphoric-hydrochloric acid composite metal catalyst, and a combination thereof. The inorganic binder may include about 0.01 parts to about 0.5 parts by weight of the acid catalyst.

The curing agent may be selected from the group consisting of aliphatic polyamine, acrylonitrile modified amine, polyamide, amidoamine, dicyandiamide, amide resin, isocyanate, melamine, and a combination thereof. The inorganic binder may include about 0.05 parts to about 1 part by weight of the curing agent.

The metallic additive may include an aluminum compound. The aluminum compound may be prepared by mixing aluminum isopropoxide with aluminum chloride. The inorganic binder may include about 0.05 parts to about 0.5 parts by weight of the metallic additive.

The photocatalyst 230 may be prepared in a liquid state in which the plurality of compositions are mixed with a predetermined solvent and coupled to the top surface part 223 of the first insulator 220.

For example, the photocatalyst 230 may be coupled to the top surface part 223 by the coating. The coating may be performed through, for example, dip coating, spray coating, screen printing, or the like. In the case of the dip coating, a drying temperature may vary according to characteristics of a coating base material, for example, the drying process may be performed at a temperature of about 148° C. to about 152° C. for about 9 minutes to about 11 minutes. As described above, the photocatalyst 230 may be produced in a liquid state and coated on the first insulator 220. Therefore, the photocatalyst 230 may be easily coupled to the surface of the insulator 220 (an adhesive force being secured).

When the photocatalyst 230 having the above-described components is provided on the top surface part 223, water ($H_2O$) or oxygen ($O_2$) may be converted into reactive oxygen species (ROS) by the catalysis of the photocatalyst 230. The reactive oxygen species include hydroxyl radical ($OH^-$), hydrogen peroxide ($H_2O_2$), and the like.

The reactive oxygen species may perform strong germicidal (oxidation) and deodorization actions. In detail, the reactive oxygen species may decompose gas pollutants, such as toluene and ammonia, as well as biological pollutants, such as bacteria or fungi composed of organic matter, into water harmless to the humans and carbon dioxide. Therefore, the photocatalyst 230 may prevent creation of pollutants resulting from air or moisture, that is, accumulation of dust or propagation of microorganisms.

The first discharge electrode 240 may be disposed on the photocatalyst 230. As described above, the first discharge electrode 240 may be printed with a metal oxide paste on the top surface of the photocatalyst 230 (S14). The first substrate 200 may be completely manufactured through the operations S11 to S14.

An operation of the above-described first substrate 200 will be described below in brief.

When a high voltage greater than a threshold voltage is applied to the first discharge electrode 240 provided with the pattern frame 243, a discharge phenomenon occurs around the ground electrode 210 and the first discharge electrode 240 due to high electric fields.

Free electrons passing around the ground electrode 210 and the first discharge electrode 240 are accelerated by the electric fields and collide with neutral molecules (oxygen and nitrogen) in the air to ionize the molecules, thereby generating a large amount of ions. In this case, the air may be air passing through the first flow holes 250. The first discharge electrode 240 may be understood as an electrode for generating ions.

After the manufacturing of the first substrate 200, the second substrate 300 may be manufactured. The second substrate 300 is disposed to be spaced downward from the first substrate 200.

In detail, the second substrate main body 301 of the second substrate 300 includes the second discharge electrode 310 acting with the ground electrode 210 to perform plasma discharge and the second insulator 320 surrounding the second discharge electrode 310 to prevent the second discharge electrode 310 from being exposed to the outside.

The second discharge electrode 310 may be formed of metal, for example, copper (Cu), and the second insulator 320 may be formed of an epoxy resin.

The second insulator 320 includes a bottom surface part 321 on which the second discharge electrode 310 is disposed, a side surface part 322 extending upward from each of both sides of the bottom surface part 321, and a top surface part 323 covering an upper side of the side surface part. An outer surface of the second discharge electrode 310 is completely surrounded by the lower, side, and top surface parts of the second insulator 320.

A method of manufacturing the second discharge electrode 310 and the second insulator 320 will be described below in brief.

The second discharge electrode 310 is masked on the bottom surface part 321 of the second insulator 320. Here, the bottom surface part 321 is formed of an epoxy resin and may be understood as a base on which the second discharge electrode 310 is disposed.

The side and top surface parts 322 and 323 of the second insulator 320 are coated on the side and top surfaces of the second discharge electrode 310 exposed to the outside. In this case, the coated side and top surface parts 322 and 323 may be formed of the same epoxy resin as the bottom surface part 321.

The photocatalyst 230, which reacts with or is activated by visible light, is disposed on the second insulator 320.

The second substrate 300 including the second discharge electrode 310 and the second insulator 320 which are manufactured in the above-described method may be disposed to be spaced a distance corresponding to the distance formation part 400 downward from the first substrate 200 (S15 and S16).

The lower, side, and top surface parts 221, 222, and 223 of the first insulator 220 may be referred to as a first base, a first side surface part, and a first top surface part, respectively. Also, the lower, side, and top surface parts 321, 322, and 323 may be referred to as a second base, a second side surface part, and a second top surface part, respectively.

An operation of the second substrate 300 including the above-described constitutions and ground electrode 210 will be described below in brief.

When a high voltage greater than a threshold voltage is applied to the second discharge electrode 310, dielectric breakdown occurs between the ground electrode 210 and the second discharge electrode 310, and a discharge phenomenon takes place due to high electric fields, thereby forming a high intensity plasma region.

Free electrons passing around the plasma region are accelerated by the electric field to react with air, and as a result, a large amount of OH radical is generated. In this case, the air may be air passing through the second flow hole 350. The second discharge electrode 310 is disposed to be spaced a distance corresponding to the distance formation part 400 from the ground electrode 210 and thus understood as a "surface discharge electrode" for generating radical ions.

In summary, the plasma electrode device according to the embodiment can generate a large amount of ions by the plasma discharge of the ground electrode and the first discharge electrode, resulting in easily removing pollutants or smells resulting from a predetermined place.

In addition, the plasma electrode device can generate a large amount of radicals by the plasma discharge (surface discharge) of the ground electrode and the second discharge electrode to easily remove smells in the air.

Further, the photocatalyst in the plasma electrode device can easily decompose the harmful substances, perform the antibacterial and germicidal functions, and reduce the ozone.

According to the embodiments, the plasma electrode device includes the first substrate provided with the first discharge electrode and the ground electrode and the second substrate provided with the second discharge electrode to generate a large amount of ions through the interaction between the first discharge electrode and the ground electrode and a large amount of radicals through the interaction between the second discharge electrode and the ground electrode.

In addition, the pollutants or smells resulting from a predetermined place can be easily removed using the large amount of ions, and smells in the air can be easily removed using the large amount of radicals.

Further, the insulator formed of an epoxy resin is disposed to surround the electrode provided as the metal plate, thereby easily generating the plasma discharge.

Furthermore, the plasma electrode device includes the photocatalyst reacting with the visible light to easily decompose the various harmful substances, perform the antibacterial and germicidal functions, and reduce the ozone.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A plasma electrode device comprising:
   a first substrate including a first substrate body and a first discharge electrode, the first substrate body having at least one first flow hole for air to flow, and the first discharge electrode is on a surface of the first substrate body; and
   a second substrate disposed on a side of the first substrate, the second substrate including at least one second flow hole for air to flow, and a second discharge electrode,
   wherein the first substrate body includes:
      a ground electrode to act with the first discharge electrode or the second discharge electrode to perform plasma discharge; and
      a first insulator to couple to the ground electrode,
      wherein the plasma electrode device further comprises a photocatalyst between the first insulator and the first discharge electrode, and the photocatalyst to activate by visible light to decompose a pollutant or reduce ozone.

2. The plasma electrode device according to claim 1, wherein the first insulator to surround the ground electrode.

3. The plasma electrode device according to claim 2, wherein the first insulator includes:
   a first base on which the ground electrode is provided;
   a first side surface part to extend from a first side and a second side of the first base, the first side surface part to cover side surfaces of the ground electrode; and
   a first top surface part to cover a top surface of the ground electrode.

4. The plasma electrode device according to claim 1, wherein the second substrate includes a second insulator to surround the second discharge electrode.

5. The plasma electrode device according to claim 4, wherein the second insulator includes:
   a second base on which the second discharge electrode is provided;
   a second side surface part to extend from a first side and a second side of the second base, the second side surface part to cover side surfaces of the second discharge electrode; and
   a second top surface part to cover a top surface of the second discharge electrode.

6. he plasma electrode device according to claim 1, further comprising a distance formation part between the first substrate and the second substrate to space the second substrate a predetermined distance from the first substrate.

7. The plasma electrode device according to claim 4, wherein the first insulator is formed of an epoxy resin.

8. The plasma electrode device according to claim 4, wherein the second insulator is formed of an epoxy resin.

9. The plasma electrode device according to claim 1, wherein the photocatalyst includes silver phosphate ($Ag_3PO_4$), titanium dioxide ($TiO_2$), and inorganic binder.

10. The plasma electrode device according to claim 1, wherein the at least one first flow hole is provided in plurality, and
    the at least one second flow hole has a same number as the plurality of the first flow holes to communicate with the plurality of first flow holes.

11. A plasma electrode device comprising:
    a first substrate including a first substrate body and a first discharge electrode, the first substrate body having at least one first flow hole for air to flow, and the first discharge electrode is on a surface of the first substrate body; and
    a second substrate disposed on a side of the first substrate, the second substrate including at least one second flow hole for air to flow, and a second discharge electrode,
    wherein the first substrate body includes:
       a ground electrode to act with the first discharge electrode or the second discharge electrode to perform plasma discharge; and
       a first insulator to couple to the ground electrode,
       wherein the first discharge electrode includes:
          a discharge electrode to receive electric power;
          a pattern frame to surround a portion of the at least one first flow hole, and the pattern frame to have a preset shape around the portion of the at least one first flow hole; and
          at least one discharge needle provided at the pattern frame.

12. A plasma electrode device comprising:
    a first substrate including a first substrate body and a first discharge electrode, the first substrate body having at least one first flow hole for air to flow, and the first discharge electrode is on a surface of the first substrate body; and
    a second substrate disposed on a side of the first substrate, the second substrate including at least one second flow hole for air to flow, and a second discharge electrode,
    wherein the first substrate body includes:
       a ground electrode to act with the first discharge electrode or the second discharge electrode to perform plasma discharge; and
       a first insulator to couple to the ground electrode, wherein the at least one first flow hole is provided in plurality, and a pattern frame is disposed to surround a portion of the plurality of first flow holes.

13. A method for providing a plasma electrode device, comprising:
   providing a first substrate by:
      providing a ground electrode on a surface part of a first insulator;
      covering the ground electrode using a side part and a top part of the first insulator;
      providing a photocatalyst on the first insulator; and
      providing a first discharge electrode on the photocatalyst.

14. The method according to claim 13, further comprising:
   providing a second substrate; and
   providing a distance formation part between the second substrate and the first substrate,
   wherein the providing of the second substrate includes:
      providing a second discharge electrode on a surface part of a second insulator; and
      covering a side surface and a top surface of the second discharge electrode with a side surface part and a top surface part of the second insulator.

15. A plasma electrode device comprising:
   a first substrate provided with a first substrate body including a ground electrode and a photocatalyst, the first substrate including a first discharge electrode on a surface of the first substrate body;
   a first insulator on the first substrate body, the first insulator to surround the ground electrode;
   a second substrate disposed on a side of the first substrate, the second substrate including a second substrate body, the second substrate including a second discharge electrode;
   a second insulator on the second substrate body, the second insulator to surround the second discharge electrode; and
   a distance formation part between the first substrate and the second substrate.

16. The plasma electrode device according to claim 15, wherein the first substrate body includes a plurality of first flow holes for air to flow, and
   the first discharge electrode is on a surface of the first substrate body.

17. The plasma electrode device according to claim 16, wherein the first discharge electrode includes:
   a discharge electrode to receive electric power;
   a plurality of pattern frames to surround portions of the plurality of first flow holes, and each of the pattern frames to have a closed shape; and
   at least one discharge needle to protrude from an outer circumferential surface of one of the pattern frames.

18. The plasma electrode device according to claim 17, wherein the pattern frame has one of a circular shape, an oval shape, and a polygonal shape.

19. The plasma electrode device according to claim 16, wherein a plurality of second flow holes are provided in the second substrate body, and locations of the plurality of second flow holes corresponding to locations of the plurality of first flow holes.

* * * * *